United States Patent
Hyung et al.

(10) Patent No.: US 10,835,405 B2
(45) Date of Patent: Nov. 17, 2020

(54) METHOD AND APPARATUS FOR WALKING ASSIST

(71) Applicant: Samsung Electronics Co., Ltd., Suwon-si (KR)

(72) Inventors: Seungyong Hyung, Yongin-si (KR); Hyun Do Choi, Yongin-si (KR); Jusuk Lee, Hwaseong-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 384 days.

(21) Appl. No.: 15/958,531

(22) Filed: Apr. 20, 2018

(65) Prior Publication Data
US 2019/0142618 A1 May 16, 2019

(30) Foreign Application Priority Data

Nov. 15, 2017 (KR) .......................... 10-2017-0152333

(51) Int. Cl.
*B25J 9/00* (2006.01)
*G16H 20/30* (2018.01)
(Continued)

(52) U.S. Cl.
CPC ......... *A61F 5/0102* (2013.01); *A61H 1/0266* (2013.01); *A61H 3/00* (2013.01);
(Continued)

(58) Field of Classification Search
CPC ............ A61H 1/0266; A61H 2201/165; A61H 2201/5007; A61H 2201/5058;
(Continued)

(56) References Cited

U.S. PATENT DOCUMENTS

| 2015/0045703 A1 | 2/2015 | Strausser et al. |
| 2016/0220438 A1 | 8/2016 | Walsh et al. |

FOREIGN PATENT DOCUMENTS

| EP | 2982350 A1 | 2/2016 |
| EP | 3 166 033 A1 | 5/2017 |

(Continued)

OTHER PUBLICATIONS

Luke M. Mooney, et al., "Autonomous exoskeleton reduces metabolic cost of human walking", Journal of Neuroengineering and Rehabilitation, 2014, 11:151, http://www.jneuroengrehab.com/content/11/1/151.

(Continued)

*Primary Examiner* — Brian A Dukert
(74) *Attorney, Agent, or Firm* — Harness, Dickey & Pierce, P.L.C.

(57) ABSTRACT

Provided is a method and device for walking assistance that may estimate a state vector of a foot of a user and a variance matrix corresponding to the state vector, adjust a probability of a contact sensor based on at least one estimate included in the estimated state vector in response to receiving a contact signal from the contact sensor, calculate a combination rate between a measurement value of an acceleration sensor and the estimated state vector based on a measurement error matrix including the adjusted probability, update the estimated state vector and the estimated variance matrix based on the calculated combination rate, determine whether the foot lands on the ground based on the updated state vector and the updated variance matrix, and change an operation mode of a walking assistance device based on a result of the determination.

22 Claims, 7 Drawing Sheets

(51) Int. Cl.
  *A61H 1/02* (2006.01)
  *A61F 5/01* (2006.01)
  *A61H 3/00* (2006.01)
  *G16H 50/20* (2018.01)

(52) U.S. Cl.
  CPC ............ *B25J 9/0006* (2013.01); *G16H 20/30* (2018.01); *G16H 50/20* (2018.01); *A61B 2562/0219* (2013.01); *A61B 2562/0252* (2013.01); *A61H 2201/164* (2013.01); *A61H 2201/165* (2013.01); *A61H 2201/1642* (2013.01); *A61H 2201/5007* (2013.01); *A61H 2201/5058* (2013.01); *A61H 2201/5061* (2013.01); *A61H 2201/5069* (2013.01); *A61H 2201/5084* (2013.01)

(58) Field of Classification Search
  CPC .... A61H 2201/5069; A61H 2201/5084; A61H 2201/5061; A61H 3/00; A61F 2/68; A61F 2/60; A61F 5/0102; A61B 2562/0219; A61B 2562/0252; B25J 9/0006
  See application file for complete search history.

(56) References Cited

FOREIGN PATENT DOCUMENTS

| | | |
|---|---|---|
| JP | 201749158 A | 3/2017 |
| KR | 101268401 B1 | 5/2013 |
| KR | 101274114 B1 | 6/2013 |
| KR | 2018-0023708 A | 3/2018 |
| WO | WO-2015/146048 A1 | 10/2015 |
| WO | WO-2015/164421 A1 | 10/2015 |

OTHER PUBLICATIONS

Steven H. Collins et al., "Reducing the energy cost of human walking using an unpowered exoskeleton", LETTER, Nature, Macmillian Publishers Limited, 2015, vol. 000, doi:10.1038/nature14288.
Extended European Search Report issued by the European Patent Office dated Feb. 18, 2019 for the corresponding EP Patent Application No. 18182719.7.

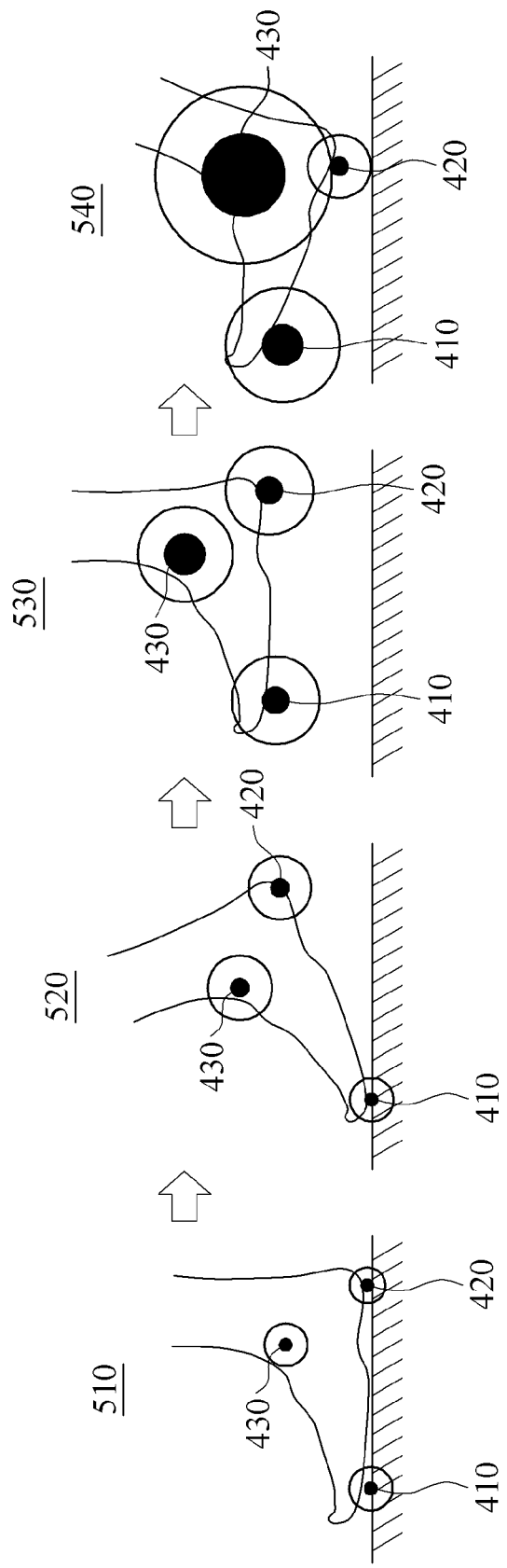

METHOD AND APPARATUS FOR WALKING ASSIST

CROSS-REFERENCE TO RELATED APPLICATION

This application claims priority under 35 U.S.C. § 119 to Korean Patent Application No. 10-2017-0152333, filed on Nov. 15, 2017, in the Korean Intellectual Property Office, the entire contents of which are incorporated herein by reference in their entirety.

BACKGROUND

1. Field

Some example embodiments relate to a method and/or device for walking assistance.

2. Description of the Related Art

Currently, an increasingly large number of people suffer from pain and discomfort due to joint issues. Accordingly, there is an increasing interest in a walking assistance device that may assist elderly people or patients having walking issues due to their uncomfortable joints.

SUMMARY

Some example embodiments relate to a walking assistance method.

In some example embodiments, the walking assistance method may include estimating a state vector of a foot of a user and a variance matrix corresponding to the state vector; adjusting, in response to receiving a contact signal from a contact sensor, a probability of the contact sensor to generate an adjusted probability based on at least one estimate included in the state vector, the adjusted probability indicating a weight given to the contact signal received from the contact sensor; calculating a combination rate between a measurement value of an acceleration sensor and the state vector based on a measurement error matrix, the measurement error matrix including the adjusted probability; updating the state vector and the variance matrix to generate an updated state vector and an updated variance matrix, respectively, based on the combination rate; determining whether the foot of the user lands on a ground based on the updated state vector and the updated variance matrix; and changing an operation mode of a walking assistance device in response determining that the foot of the user lands on the ground.

In some example embodiments, the adjusting of the probability includes performing an operation based on an estimate associated with a velocity of the foot in each of a first direction and a second direction among estimates included in the state vector; and changing the probability of the contact sensor by a first error variance associated with the contact sensor based on a result of the operation.

In some example embodiments, the changing the probability changes the probability such that the probability of the contact sensor decreases.

In some example embodiments, the method further includes further changing the probability by a second error variance in response to not receiving the contact signal from the contact sensor after changing the probability of the contact sensor by the first error variance.

In some example embodiments, the determining includes determining that the foot of the user lands on the ground, in response to (i) an estimate associated with a velocity of the foot among estimates included in the updated state vector being less than a threshold velocity value and (ii) a probability of the estimate associated with the velocity among probabilities included in the updated variance matrix being less than a threshold probability.

In some example embodiments, the estimating estimates the state vector such that the state vector includes an estimate for each of a velocity of the foot in each of a first direction and a second direction, an acceleration of the foot in each of the first direction and the second direction, an angle between the foot and the ground, and an angular velocity of the foot, and the updating updates the state vector such that the updated state vector includes a result of updating each estimate included in the state vector.

In some example embodiments, the variance matrix includes an estimation error covariance of each estimate in the state vector, and the updated variance matrix includes a result of updating each estimation error covariance.

In some example embodiments, each estimation error covariance represents a confidence of a corresponding estimate in the state vector.

In some example embodiments, the measurement error matrix further includes (i) a measurement error variance associated with a measurement accuracy of an acceleration of the foot in each of a first direction and a second direction and (ii) an error variance associated with a measurement accuracy of an angular velocity of the foot in each of the first direction and the second direction.

In some example embodiments, the method further includes generating, by the contact signal, the contact signal in response to a pressure being applied to the contact sensor.

Some example embodiments relate to a non-transitory computer-readable storage medium including instructions that, when executed by a processor, cause the processor to perform the walking assistance method.

Some example embodiments relate to a walking assistance device.

In some example embodiment, the walking assistance device may include at least one contact sensor; an acceleration sensor; and a controller configured to, estimate a state vector of a foot of a user and a variance matrix corresponding to the state vector, adjust, in response to receiving a contact signal from the at least one contact sensor, a probability of the at least one contact sensor to generate an adjusted probability based on at least one estimate included in the estimated state vector, the adjusted probability indicating a weight given to the contact signal received from the at least one contact sensor, calculate a combination rate between a measurement value of an acceleration sensor and the state vector based on a measurement error matrix, the measurement error matrix including the adjusted probability, update the state vector and the variance matrix to generate an updated state vector and an updated variance matrix, respectively, based on the combination rate, determine whether the foot of the user lands on a ground based on the updated state vector and the updated variance matrix, and change an operation mode of the walking assistance device in response determining that the foot of the user lands on the ground.

In some example embodiment, the controller is configured to, perform an operation based on an estimate associated with a velocity of the foot in each of a first direction and a second direction among estimates included in the state vector, and change the probability of the at least one contact sensor by a first error variance associated with the at least one contact sensor based on a result of the operation.

In some example embodiment, the controller is configured to change the probability such that the probability of the at least one contact sensor deceases.

In some example embodiment, the controller is configured to further change the probability by a second error variance in response to not receiving the contact signal from the at least one contact sensor after changing the probability of the at least one contact sensor by the first error variance.

In some example embodiment, the controller is configured to determine that the foot lands on the ground, if (i) an estimate associated with a velocity of the foot among estimates included in the updated state vector is less than a threshold velocity value and (ii) a probability of the estimate associated with the velocity among probabilities included in the updated variance matrix is less than a threshold probability.

In some example embodiment, the controller is configured to estimate the state vector such that the state vector includes an estimate for each of a velocity of the foot in each of a first direction and a second direction, an acceleration of the foot in each of the first direction and the second direction, an angle between the foot and the ground, and an angular velocity of the foot, and update the state vector such that the updated state vector includes a result of updating each estimate included in the state vector.

In some example embodiment, the variance matrix includes an estimation error covariance of each estimate in the state vector, and the updated variance matrix includes a result of updating each estimation error covariance.

In some example embodiment, each estimation error covariance represents a confidence of a corresponding estimate in the state vector.

In some example embodiment, the measurement error matrix further includes (i) a measurement error variance associated with a measurement accuracy of an acceleration of the foot in each of a first direction and a second direction and (ii) an error variance associated with a measurement accuracy of an angular velocity of the foot in each of the first direction and the second direction.

In some example embodiment, the at least one contact sensor is configured to generate the contact signal in response to a pressure being applied to the at least one contact sensor.

In some example embodiment, the acceleration sensor is configured to measure an acceleration and an angular velocity of the foot.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which:

FIG. 5 illustrates an example of describing a change in an estimation error covariance according to at least one example embodiment;

DETAILED DESCRIPTION

Figure 1:
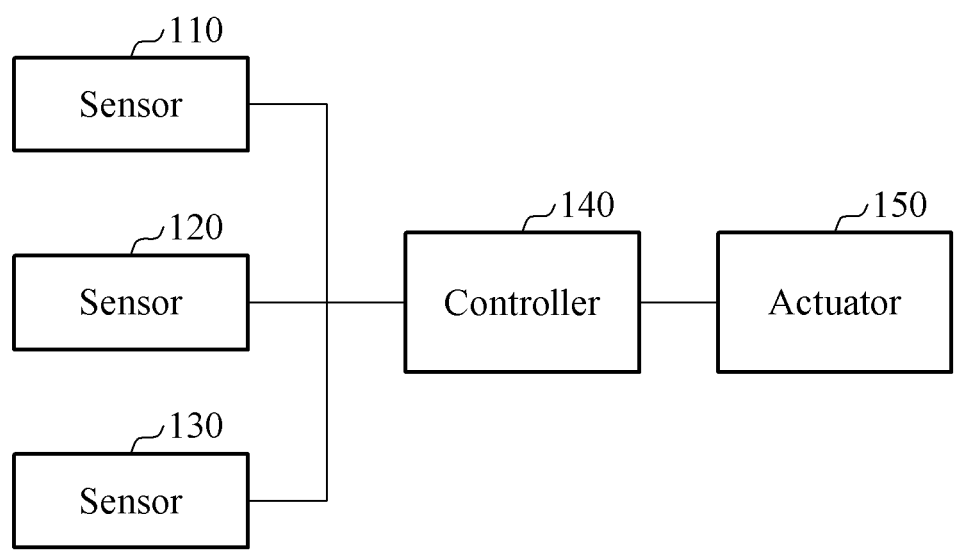
FIGS. 1 through 3 illustrate a walking assistance device according to at least one example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of example embodiments, detailed description of well-known related structures or functions will be omitted when it is deemed that such description will cause ambiguous interpretation of the present disclosure.

It should be understood, however, that there is no intent to limit example embodiments to the particular example embodiments disclosed herein. On the contrary, the example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The terminology used herein is for the purpose of describing particular example embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined herein, all terms used herein including technical or scientific terms have the same meanings as those generally understood by one of ordinary skill in the art. Terms defined in dictionaries generally used should be construed to have meanings matching with contextual meanings in the related art and are not to be construed as an ideal or excessively formal meaning unless otherwise defined herein.

Figure 2:
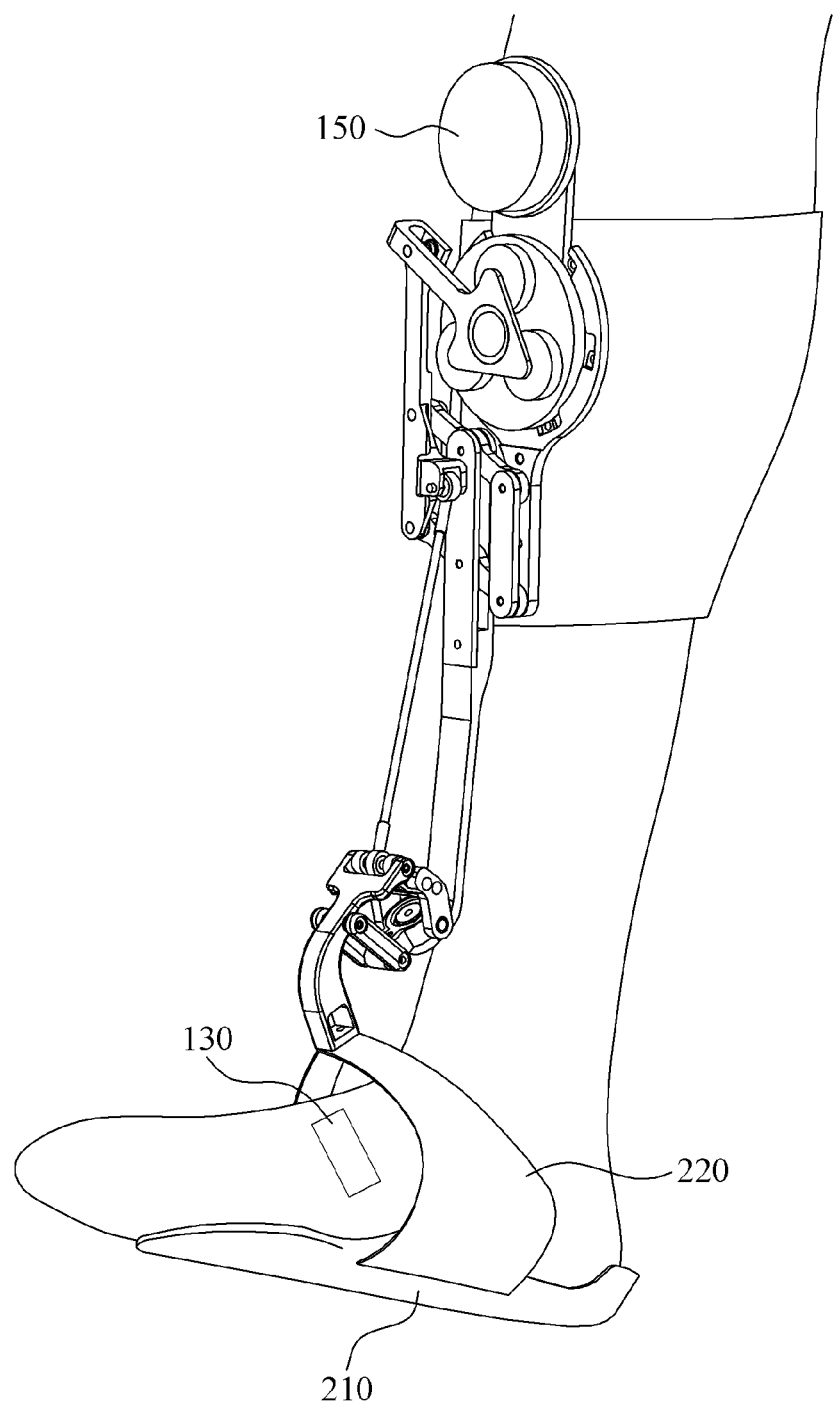
Figure 3:
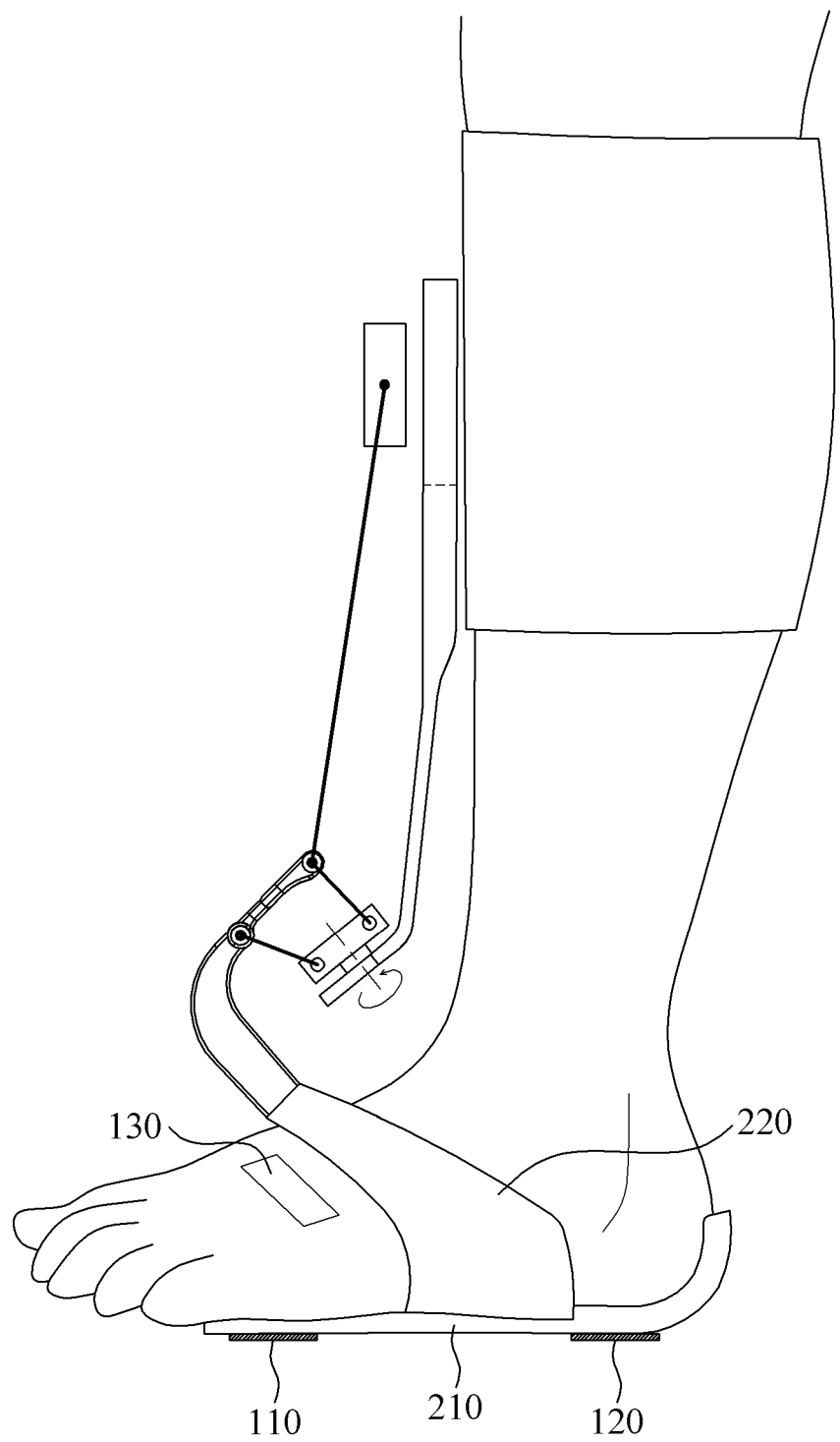

FIGS. 1 through 3 illustrate a walking assistance device according to at least one example embodiment.

Referring to FIG. 1, a walking assistance device 100 includes a plurality of sensors 110, 120, and 130, a controller 140, and an actuator 150.

The walking assistance device 100 may be worn by a user and assists a motion or walking, for example, a gait of the user.

Referring to FIGS. 2 and 3, the walking assistance device 100 may be provided around an ankle of the user and may assist walking of the user or a motion of the ankle. Further, the walking assistance device 100 may assist another portion of an upper body, for example, a wrist, an elbow, and a shoulder, of the user, or another portion of a lower body, for example, a knee and a hip joint, of the user. Hereinafter, an example in which the walking assistance device 100 assists walking of a user or a motion of an ankle will be described.

Each of the sensor 110 and the sensor 120 may generate a contact signal in response to a contact with, for example, a ground, and may transmit the contact signal to the controller 140.

For example, the sensor 110 may be a contact sensor, for example, a force sensitive resistor (FSR) sensor, and may be provided on one side, for example, a toe portion, of a sole of a foot frame 210 of the walking assistance device 100 as shown in FIG. 3. The sensor 110 may transmit a contact signal to the controller 140 in response to a pressure being applied to the sensor 110. The sensor 120 may be a contact sensor and may be provided on another side, for example, a heel portion of the sole of the foot frame 210 as shown in FIG. 3. The sensor 120 may transmit a contact signal to the controller 140 in response to a pressure being applied to the sensor 120. A location of each of the sensors 110 and 120, a number thereof, and a type thereof are provided as examples only and are not limited thereto.

The sensor 130 may measure an acceleration and an angular velocity of a foot and transmit measurement values to the controller 140. Referring to FIGS. 2 and 3, the sensor 130 may be provided on the top of the foot. As another example, the sensor 130 may be attached to a portion 220 that covers an ankle. The sensor 130 may be, for example, an inertial measurement units (IMU) sensor. A location of the sensor 130, a number thereof, and a type thereof are provided as examples only and are not limited thereto.

The controller 140 may include a memory and processing circuitry (not shown).

The memory (not shown) may include at least one of a volatile memory, non-volatile memory, random access memory (RAM), a flash memory, a hard disk drive, and an optical disk drive.

The processing circuitry may be, but not limited to, a processor, Central Processing Unit (CPU), a controller, an arithmetic logic unit (ALU), a digital signal processor, a microcomputer, a field programmable gate array (FPGA), an Application Specific Integrated Circuit (ASIC), a System-on-Chip (SoC), a programmable logic unit, a microprocessor, or any other device capable of performing operations in a defined manner.

The processing circuitry of the controller 140 may be configured, through a layout design or execution of computer readable instructions stored in a memory (not shown), as a special purpose computer to estimate a state vector of the foot and a covariance matrix corresponding to the state vector, perform a probability adjustment, and update the estimated state vector and covariance matrix based on a filter. Here, the filter may be a linear filter, a Kalman filter, an extended Kalman filter, or a particle filter. The operation of the controller 140 performing estimation, probability adjustment, and update will be described with reference to FIG. 4A.

Further, processing circuitry of the controller 140 may be configured to determine whether the foot of the user lands on the ground based on the updated state vector and the updated covariance matrix, and change an operation mode of the walking assistance device 100 based on the determination.

A "swing phase" refers to a state of a first leg moving a desired (or, alternatively, a predetermined) angle forward in a walking cycle. A "stance phase" refers to a state of the first leg being in contact with the ground and supporting a body in the walking cycle. For example, a swing phase torque may correspond to a flexion torque in a direction in which a joint bends, and a stance phase torque may correspond to an extension torque in a direction in which a joint stretches.

In response to determining that the foot of the user lands on the ground, the controller 140 may change a current operation mode of the walking assistance device 100 from a swing mode to assist the swing phase to a stance mode to assist the push-off motion in the stance phase.

In the stance mode, the controller 140 may control the actuator 150 so that the walking assistance device 100 may perform a push-off operation of pushing off the ground. For example, the controller 140 may supply power to the actuator 150 to rotate the ankle joint of the user in a clockwise direction so that the assistance device pushes the ground while providing a force to a longitudinal member (not shown), thereby assisting a push-off motion of the user.

Further, in response to determining that the foot of the user does not land on the ground, the controller 140 may maintain the swing mode that is a current operation mode, and may control the actuator 150 so that the walking assistance device 100 may assist a dorsi flexion motion of the user such that dorsal of the foot of the user flexes towards the leg of the user.

Accordingly, the controller 140 may improve the functioning of the walking assistance apparatus 100 itself by enhancing a landing recognition rate of the walking assistance device 100 and increasing an accuracy of a point in time at which an ankle assistance torque is to be applied.

Figure 4A:
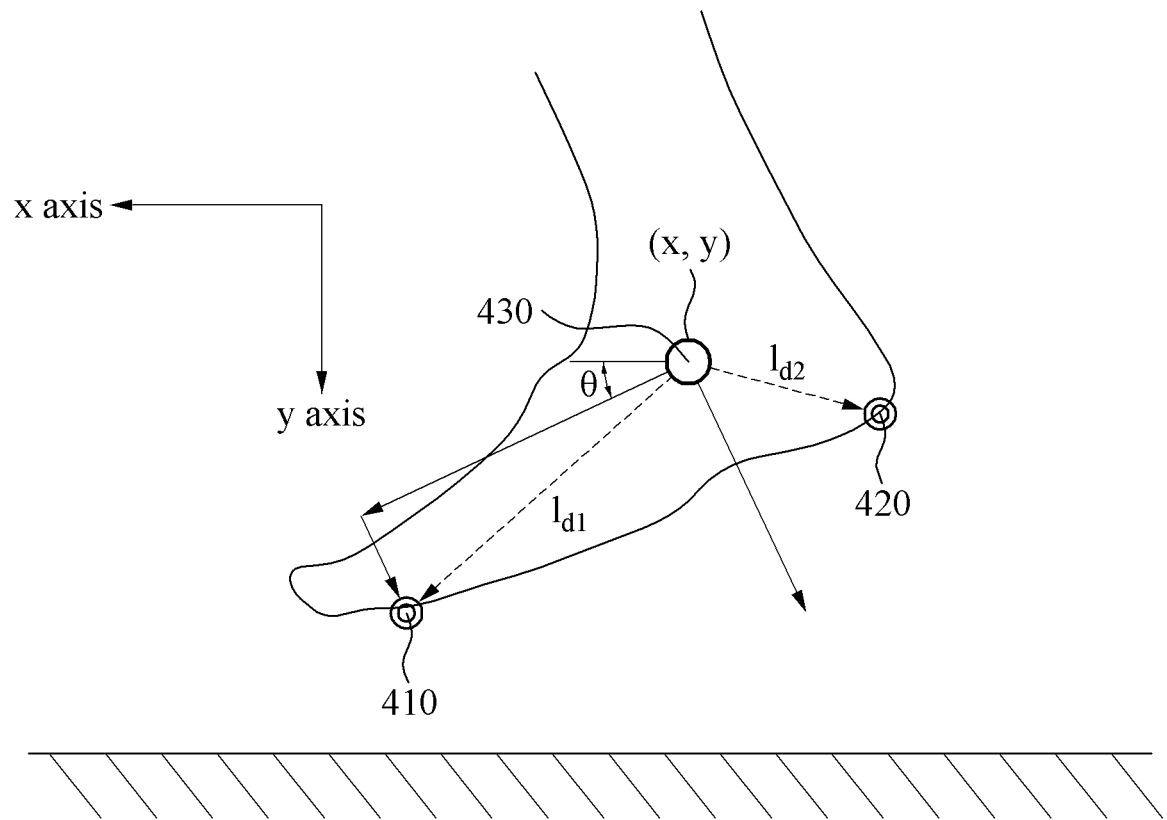
FIGS. 4A and 4B illustrate an example of an operation of a walking assistance device according to at least one example embodiment.
Figure 4B:
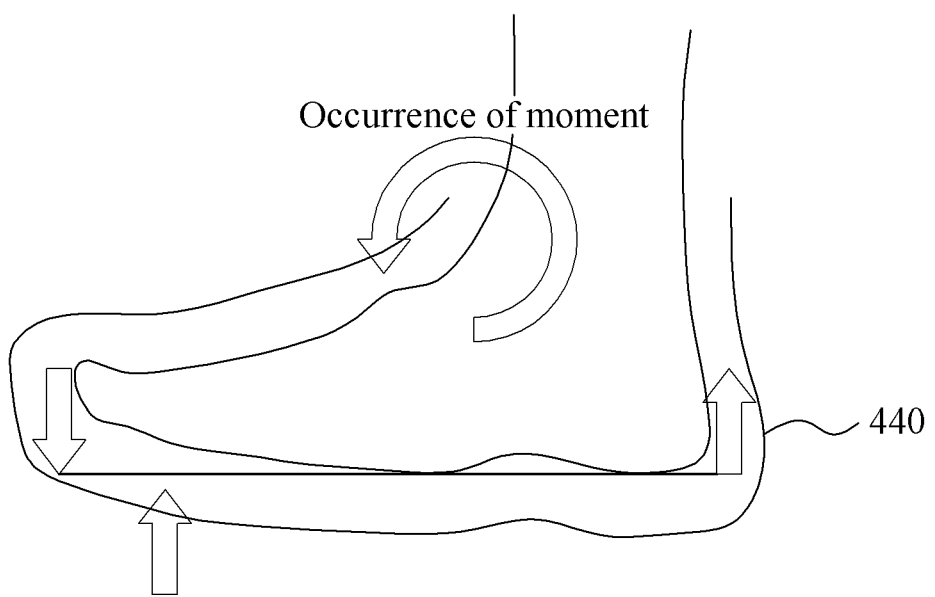

FIGS. 4A and 4B illustrate an example of an operation of a walking assistance device according to at least one example embodiment.

Referring to FIG. 4A, a foot of a user is illustrated. In an example illustrated in FIG. 4A, in which the user is assumed to wear the walking assistance device 100 around the foot, a point 410 may correspond to a location of the sensor 110 of FIG. 3, a point 420 may correspond to a location of the sensor 120, and a point 430 may correspond to a location of the sensor 130.

Prior to describing an operation of the walking assistance device 100, variables of the walking assistance device 100 are described with reference to Table 1 and Table 2.

TABLE 1

| State variables | Definition |
| --- | --- |
| $V_x$ | Velocity of foot or point 430 in x-axial direction |
| $\dot{V}_x$ | Acceleration of foot or point 430 in x-axial direction |
| $V_y$ | Velocity of foot or point 430 in y-axial direction |
| $\dot{V}_y$ | Acceleration of foot or point 430 in y-axial direction |
| $\theta$ | Angle between foot or point 430 and ground |
| $\dot{\theta}$ | Angular velocity of foot or point 430 |

TABLE 2

| Measurement or observation variables | Definition |
| --- | --- |
| $a_x$ | Acceleration of foot or point 430 in x-axial direction |
| $a_y$ | Acceleration of foot or point 430 in y-axial direction |
| $y_\theta$ | Angular velocity of foot or point 430 |
| $d_1$ | Velocity of first point 410 of foot |
| $d_2$ | Velocity of second point 420 of foot |

The state variables of Table 1 correspond to estimation targets of the controller 140 and the measurement variables of Table 2 correspond to estimation or observation targets of at least one of the sensors 110, 120, and 130.

The state variables and the measurement variables have relations as expressed by Equation 1.

$$a_x = \dot{V}_x \cos\theta - (\dot{V}_y + g)\sin\theta$$

$$a_y = \dot{V}_x \cos\theta + (\dot{V}_y + g)\cos\theta$$

$$y_\theta = \dot{\theta}$$

$$d_1 = \sqrt{(V_x^2 + V_y^2)} + l_{d1}\dot{\theta}$$

$$d_2 = \sqrt{(V_x^2 + V_y^2)} + l_{d2}\dot{\theta} \quad [\text{Equation 1}]$$

A function h induced from the relations of Equation 1 may be used during an update process.

Hereinafter, each of the estimation, the probability adjustment, and the update will be described.

Estimation of a State Vector and a Covariance Matrix.

The controller 140 may estimate or predict a state vector of a foot of the user and a variance matrix corresponding to the state vector. Here, the estimated state vector may include an estimate of each of the state variables described with Table 1 and the estimated variance matrix may include a probability representing a confidence of an estimate of each of the state variables. That is, the controller 140 may estimate the state variables and a probability of each of the state variables.

For example, the controller 140 may estimate a state vector $x_k$ of the foot at a point in time k based on a state vector $x_{k-1}$ at a point in time k−1, and may estimate a variance matrix $M_{k|k-1}$ at the point in time k based on a variance matrix $M_{k-1|k-1}$ at the point in time k−1. The estimation may be represented by, for example, Equation 2.

$$x_k = Ax_{k-1} \quad [\text{Equation 2}]$$

$$M_{k|k-1} = AM_{k-1|k-1}A^T + Q$$

$$A = \begin{bmatrix} 1 & \Delta t & & & & \\ & 1 & & & 0 & \\ & & 1 & \Delta t & & \\ & & & 1 & & \\ & 0 & & & 1 & \Delta t \\ & & & & & 1 \end{bmatrix}$$

In Equation 2, $x_k = [V_{x\_k} \dot{V}_{x\_k} V_{y\_k} \dot{V}_{x\_k} \theta_k \dot{\theta}_k]$. Also, A denotes a state transition matrix and Q denotes an error or noise.

$M_{k|k-1}$ includes a probability of each of the estimates included in $x_k$. The probability may also be represented as an estimation error covariance representing a confidence or uncertainty of a corresponding estimate. For example, if a probability or an estimate error covariance of $V_{y\_k}$ included in $x_k$ is relatively small, it may indicate that uncertainty of $V_{y\_k}$ is relatively low or that confidence of $V_{y\_k}$ is relatively high.

Adjustment of Sensor Probability.

During the aforementioned estimation operation, the controller 140 may receive a contact signal from the sensor 110 and/or the sensor 120. In this case, the controller 140 may adjust a probability of the sensor 110 and/or the sensor 120 based on at least one estimate included in the estimated state vector. Here, the probability of each of the sensor 110 and the sensor 120 is associated with an accuracy of each of the sensor 110 and the sensor 120, which will be described with reference to Equation 3.

For example, in response to receiving a contact signal from the sensor 110 at the point in time k, the controller 140 may perform an operation based on $V_{x\_k}$ and $V_{y\_k}$ included in $x_k$, and may apply or reflect an operation result to a first error variance set (or, alternatively, preset) for the sensor 110. The controller 140 may adjust or change the first error variance to which the operation result is applied based on the probability of the sensor 110. In a similar manner, in response to receiving a contact signal from the sensor 120 at the point in time k, the controller 140 may adjust the probability of the sensor 120. The probability adjustment may be represented by, for example, Equation 3.

$$R_{d1} = \begin{cases} (V_{x\_k}^2 + V_{y\_k}^2)\sigma_{low}^2 & \text{sensor}(110) \text{ on} \\ \sigma_{high}^2 & \text{sensor}(110) \text{ off} \end{cases} \quad [\text{Equation 3}]$$

$$R_{d2} = \begin{cases} (V_{x\_k}^2 + V_{y\_k}^2)\sigma_{low}^2 & \text{sensor}(110) \text{ on} \\ \sigma_{high}^2 & \text{sensor}(110) \text{ off} \end{cases}$$

In Equation 3, $R_{d1}$ denotes the probability of the sensor 110 and $R_{d2}$ denotes the probability of the sensor 120. Differently representing, $R_{d1}$ may denote a measurement error variance representing an inaccuracy of the sensor 110 or the measurement variable $d_1$ of Table 2, and $R_{d2}$ may denote a measurement error variance representing an inaccuracy of the sensor 120 or the measurement variable d2 of Table 2. Here, if the measurement error variance increases, it indicates that the accuracy decreases. Also, in Equation 3, $\sigma_{low}^2$ denotes the first error variance and $\sigma_{high}^2$ denotes a second error variance set (or, alternatively, preset) for each of the sensor 110 and the sensor 120 and is greater than $\sigma_{low}^2$.

As an example of Equation 3, if no contact signal is received from each of the sensor 110 and the sensor 120, each of $R_{d1}$ and $R_{d2}$ is $\sigma_{high}^2$. In response to receiving a contact signal from each of the sensor 110 and the sensor 120, the controller 140 may adjust $R_{d1}$ from $\sigma_{high}^2$ to $(V_{x\_k}^2 + V_{y\_k}^2)\sigma_{low}^2$, and may adjust $R_{d2}$ from $\sigma_{high}^2$ to $(V_{x\_k}^2 + V_{y\_k}^2)\sigma_{low}^2$. Since $\sigma_{low}^2$ is less than $\sigma_{high}^2$, $R_{d1}$ and $R_{d2}$ are adjusted to decrease in response to recognizing a contact from each of the sensor 110 and the sensor 120.

The controller 140 generates a measurement error matrix that includes the adjusted probability. Once all of $R_{d1}$ and $R_{d2}$ are adjusted, the measurement error matrix includes the adjusted $R_{d1}$ and $R_{d2}$. Equation 4 shows an example of the measurement error matrix.

$$R_k = \begin{bmatrix} R_{ax} & & & & \\ & R_{ay} & & & \\ & & R_{\dot\theta} & & \\ & & & R_{d1} & \\ & & & & R_{d2} \end{bmatrix}. \text{ Here,} \quad \text{[Equation 4]}$$

$$R_{ax} = \sigma^2_{imu\_acc}$$

$$R_{ay} = \sigma^2_{imu\_acc}$$

$$R_{\dot\theta} = \sigma^2_{imu\_ang}$$

In Equation 4, $R_k$ denotes the measurement error matrix.

Also, in Equation 4, the measurement error matrix may include $R_{ax}$, $R_{ay}$, and $R_{\dot\theta}$ that represent probabilities or measurement error variances associated with a measurement accuracy of the sensor 130. Describing each of $R_{ax}$, $R_{ay}$, and $R_{\dot\theta}$ in detail, $R_{ax}$ denotes a measurement accuracy of the sensor 130 with respect to the measurement variable $a_x$ of Table 2, $R_{ay}$ denotes a measurement accuracy of the sensor 130 with respect to the measurement variable $a_y$, and $R_{\dot\theta}$ denotes a measurement accuracy of the sensor 130 with respect to the measurement variance $y_{\dot\theta}$.

In Equation 4, $\sigma^2_{imu\_acc}$, $\sigma^2_{imu\_acc}$, and $\sigma^2_{imu\_arg}$ set for $R_{ax}$, $R_{ay}$, and $R_{\dot\theta}$, respectively, denote constants.

Updating the Estimated State Vector and Covariance Matrix.

The controller 140 calculates a combination rate between $x_k$ and the measurement value of the sensor 130 based on the measurement error matrix $R_k$. For example, the controller 140 may calculate a combination rate $K_k$ at the point in time k according to Equation 5.

$$S_k = H_k M_{k|k-1} H_k^T + R_k$$

$$K_k = M_{k|k-1} H_k^T S_k^{-1} \quad \text{[Equation 5]}$$

In Equation 5, $H_k$ denotes a measurement or observation matrix at the point in time k and may be calculated according to $$H_k = \left.\frac{\partial h}{\partial x}\right|_{x=x_k}.$$

Here, the function h may be induced from the relations of Equation 1.

The combination rate represents a level at which $x_k$ and the measurement value are applied during a process of updating $x_k$. If the combination rate is relatively great, an application rate of the measurement value decreases and an application rate of $x_k$ increases during the process of updating $x_k$. Also, the combination rate may be represented as an optimal gain of a Kalman filter.

The controller 140 updates the state vector $x_k$ and the variance matrix $M_{k|k-1}$ based on the calculated combination rate. For example, the controller 140 updates the state vector $x_k$ and the variance matrix $M_{k|k-1}$ according to Equation 6.

$$\hat{x}_k = x_k + K_k(y_k - h(x_k))$$

$$M_k = (I - K_k H_k) M_{k|k-1} \quad \text{[Equation 6]}$$

In Equation 6, $\hat{x}_k$ denotes an update result of $x_k$ and $M_k$ denotes an update result of $M_{k|k-1}$. That is, $\hat{x}_k$ includes updated estimates and may be represented as $\hat{x}_k = [\hat{V}_{x\_k} \hat{V}_{x\_k} \hat{V}_{y\_k} \hat{V}_{y\_k} \hat{\theta}_k \hat{\dot\theta}_k]$. $M_k$ includes updated probabilities. Here, each of the updated probabilities may represent a confidence or uncertainty of each of the updated estimates. The confidence or uncertainty varies during walking of the user and will be described with reference to FIG. 5.

In Equation 6, $y_k$ includes a result of measuring the observation variables of Table 2. For example, referring to $y_k = [a_{a\_k} a_{y\_k} \dot\theta_k 0 0]^T$, $y_k$ may include a result of measuring, by the sensor 130, an acceleration of the foot in an x-axial direction, an acceleration of the foot in an y-axial direction, and an angular velocity of the foot.

Determining a Contact with the Ground.

The controller 140 may determine whether the foot of the user lands on the ground based on the updated state vector $\hat{x}_k$ and the updated variance matrix $M_k$. For example, if an estimate, for example, $\hat{V}_{y\_k}$, associated with a velocity of the foot among the updated estimates of $\hat{x}_k$ is less than a threshold velocity value and a probability, for example, $\hat{V}_{y\_k}$ of the estimate associated with the velocity of the foot among the probabilities included in $M_k$ is less than a threshold probability, the controller 140 may determine that the foot of the user lands on the ground. In response to determining that the foot of the user lands on the ground, the controller 140 may change an operation mode of the walking assistance device 100 to a stance mode.

The controller 140 may iteratively perform the aforementioned estimation, probability adjustment, update, and ground contact determination during walking, for example, a gait of the user.

Depending on example embodiments, if the user wearing the walking assistance device 100 walks with a shoe 440, the shoe 440 may push the sensor 110 and/or the sensor 120. For example, referring to FIG. 4B, a moment may occur during walking and a gait of the user and the shoe 440 may push the sensor 110 and/or the sensor 120 by the moment. In this case, the sensor 110 and/or the sensor 120 may inadvertently transmit a contact signal to the controller 140. That is, the contact signal may be generated in response to a contact by an object, for example, the shoe 440, instead of a contact by landing.

If a walking assistance device determines that the user lands on the ground using only the contact signal, the walking assistance device may inadvertently change the operation mode from a swing mode to a stance mode. That is, due to an inaccurate landing recognition, a malfunction of the walking assistance device may occur. In contrast, in one or more example embodiments, in response to receiving a contact signal from the sensor 110 and/or the sensor 120, the controller 140 may perform the aforementioned probability adjustment, update, and ground contact determining process, and, thus, may perform accurate landing recognition.

FIG. 5 illustrates an example of describing a change in an estimation error covariance according to at least one example embodiment.

Referring to FIG. 5, FIG. 5 illustrates gait states, for example, a first state 510, a second state 520, a third state 530, and a fourth state 540.

In each of the walking states, for example, the first state 510, the second state 520, the third state 530, and the fourth state 540, a circle indicates an estimation error covariance representing a confidence or uncertainty of an estimate of a state variable. That is, the circle visually represents a probability in the covariance matrix M.

A circle of each of the points 410, 420, and 430 gradually increases with getting closer to the third state 530 after going through the first state 510 and the second state 520. That is, as the gait state approaches the third state 530 through the first state 510 and the second state 520, an estimation error covariance of an estimate of each of the state variables is accumulated. Due to the accumulation, the uncertainty of the estimate of each of the state variables increases. The increase in the uncertainty is represented using the increasing radius of the circle. While a gait state of the user develops from the first state 510 to the third state 530, the uncertainty of the estimate of each of the state variables is great although a contact signal is generated in each of the first sensor 110 and the second sensor 120. Accordingly, the controller 140 may maintain an operation mode of the walking assistance device 100 to be in a swing mode even if the controller 140 inadvertently receives the contact signal from the first sensor 110 and/or the second sensor 110. In detail, since the estimation error variance of the estimate of $V_y$ is relatively great, the controller 140 may maintain the operation mode of the walking assistance device 100 to be in the swing mode.

The gait state of the user may enter into the first state 510 after going through the third state 530 and the fourth state 540. In the first state 510, each circle has a relatively small radius. Due to the aforementioned probability adjustment process, the estimation error variance of the estimate of each of the state variables in the first state 510 decreases. If a contact signal of each of the first sensor 110 and the second sensor 120 is generated in the first state 510, an operation mode of the walking assistance device 100 may be changed from the swing mode to the stance mode due to the relatively small uncertainty of the estimate of each of the state variables. In detail, since the estimation error variance of the estimate of $V_y$ is relatively small, the operation mode of the walking assistance device 100 may be changed to the stance mode.

Figure 6:
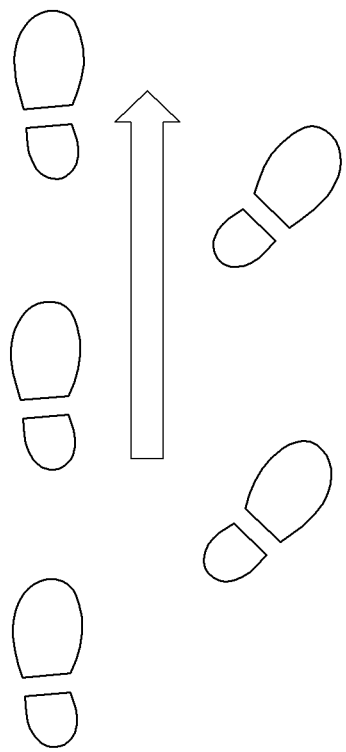
FIG. 6 illustrates another example of an operation of a walking assistance device according to at least one example embodiment.

FIG. 6 illustrates another example of an operation of a walking assistance device according to at least one example embodiment.

Referring to FIG. 6, a user may have difficulty in normally walking. That is, the user may abnormally walk. For example, as illustrated in FIG. 6, the user may not readily bend a knee and may do a circumduction gait that circumducts the entire leg.

If the user does a circumduction gait, an xy plane vector may be used instead of using a vector in an x-axial direction. For example, the aforementioned state variable $V_x$ may be replaced with a state variable $V_{new}=\sqrt{V_x^2+V_y^2}$. The controller 140 may perform the aforementioned estimation, probability, adjustment, update, and ground contact determination using $V_{new}=\sqrt{V_x^2+V_y^2}$ instead of using $V_x$.

Figure 7:
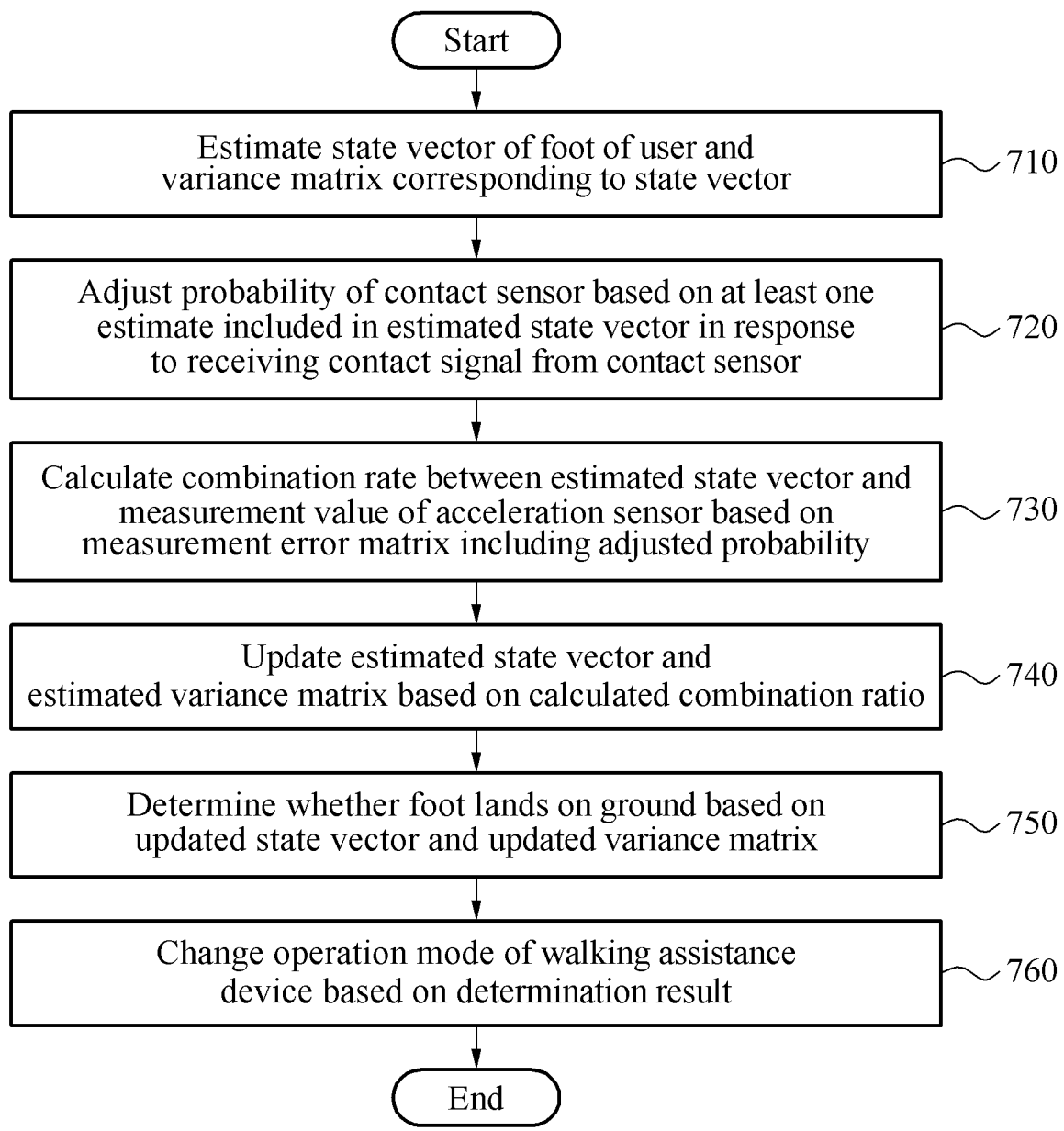
FIG. 7 is a flowchart illustrating a walking assistance method according to at least one example embodiment.

FIG. 7 is a flowchart illustrating a walking assistance method according to at least one example embodiment.

Referring to FIG. 7, in operation 710, the walking assistance device 100 estimates a state vector of a foot of a user and a variance matrix corresponding to the state vector. For example, the controller 140 of the walking assistance device 100 may estimate the state vector $x_k$ and the variance matrix $M_{k|k-1}$ corresponding to the state vector based on Equation 2. Further, in some example embodiments, the controller 140 may replace the state variables included in the state vector $x_k$ defined in an x-axial direction with state variables in an xy plane, if the user does a circumduction gait.

In operation 720, the walking assistance device 100 adjusts a probability of a contact signal based on at least one estimate included in the state vector in response to receiving a contact signal from the contact sensor, where the contact sensor may correspond to the sensor 110 and/or the sensor 120. For example, the controller 140 of the walking assistance device 100 may adjust the probability $R_{d1}$ and $R_{d2}$ of the contact signal based on Equation 3.

In some example embodiments, the controller 140 may utilize different ones of the contact sensors 110, 120 to accurately detect whether the foot contacts the ground since the center of pressure of the foot of the user with respect to the ground may shift sequentially from the heel to the forefront during a gait cycle.

In operation 730, the walking assistance device 100 calculates a combination rate between the estimated state vector and a measurement value of an acceleration sensor based on a measurement error matrix including the adjusted probability, where the acceleration sensor may correspond to the sensor 130. For example, the controller 140 of the walking assistance device 100 may generate the measurement error matrix $R_k$ based on Equation 4, and may calculate the combination rate $K_k$ based on Equation 5.

In operation 740, the walking assistance device 100 updates the estimated state vector and the estimated variance matrix based on the calculated combination rate. For example, the controller 140 of the walking assistance device 100 may update the estimated state vector $\hat{x}_k$ and the estimated variance matrix $M_k$ based on Equation 6.

In operation 750, the walking assistance device 100 determines whether the foot lands on the ground based on the updated state vector and the updated variance matrix.

In some example embodiments, the walking assistance device 100 may further increase the accuracy of detecting whether the foot of the user lands on the ground by sensing vibration occurring when the foot touches the ground using an inertial measurement unit (IMU) or acceleration sensor, for example, the sensor 130.

In still some other example embodiments, the sensors 120, 130 may generate the contact signal such that an intensity of the contact signal is proportional to the applied pressure, and the controller 140 may further increase the accuracy of detecting whether the foot of the user lands on the ground by evaluating the intensity of the contact signal.

In some example embodiments, in addition to determining whether the foot of the user is in contact with the ground, the walking assistance device 100 may further determine whether the user is wearing the walking assistance device 100 and/or whether the user is standing based on the contact signal from the contact sensor.

In operation 760, the walking assistance device 100 changes or maintains an operation mode of the walking assistance device 100 based on a result of the determination in operation 750.

In some example embodiments, in addition applying the ankle assistance torque to assist the push-off motion when the operating mode is the stance mode, the controller 140 may control vibration elements embedded in the shoe 440 of the user to haptically provide information to the user regarding, for example, a level and/or timing of the ankle assistance torque, and the accuracy of this information that is haptically provided may increase due to the aforementioned determination.

The walking assistance device 100 may repeatedly perform operations 710 through 760 during walking, for example, a gait, of the user and may assist walking of the user with an assistance force at an optimal point in time.

Descriptions made above with reference to FIGS. 1 through 6 may be applicable to FIG. 7 and a further description is omitted.

The units and/or modules described herein may be implemented using hardware components, software components, and/or combinations thereof. For example, the hardware components may include microphones, amplifiers, band-pass filters, audio to digital convertors, and processing devices. A processing device may be implemented using one or more hardware device configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

Example embodiments of the inventive concepts having thus been described, it will be obvious that the same may be varied in many ways. Such variations are not to be regarded as a departure from the intended spirit and scope of example embodiments of the inventive concepts, and all such modifications as would be obvious to one skilled in the art are intended to be included within the scope of the following claims.

What is claimed is:

1. A walking assistance method comprising:
   estimating a state vector of a foot of a user and a variance matrix corresponding to the state vector;
   adjusting, in response to receiving a contact signal from a contact sensor, a probability of the contact sensor to generate an adjusted probability based on at least one estimate included in the state vector, the adjusted probability indicating a weight given to the contact signal received from the contact sensor;
   calculating a combination rate between a measurement value of an acceleration sensor and the state vector based on a measurement error matrix, the measurement error matrix including the adjusted probability;
   updating the state vector and the variance matrix to generate an updated state vector and an updated variance matrix, respectively, based on the combination rate;
   determining whether the foot of the user lands on a ground based on the updated state vector and the updated variance matrix; and
   changing an operation mode of a walking assistance device in response determining that the foot of the user lands on the ground.

2. The method of claim 1, wherein the adjusting of the probability comprises:
   performing an operation based on an estimate associated with a velocity of the foot in each of a first direction and a second direction among estimates included in the state vector; and
   changing the probability of the contact sensor by a first error variance associated with the contact sensor based on a result of the operation.

3. The method of claim 2, wherein the changing the probability changes the probability such that the probability of the contact sensor decreases.

4. The method of claim 2, further comprising:
   further changing the probability by a second error variance in response to not receiving the contact signal from the contact sensor after changing the probability of the contact sensor by the first error variance.

5. The method of claim 1, wherein the determining comprises:
   determining that the foot of the user lands on the ground, in response to (i) an estimate associated with a velocity of the foot among estimates included in the updated state vector being less than a threshold velocity value and (ii) a probability of the estimate associated with the velocity among probabilities included in the updated variance matrix being less than a threshold probability.

6. The method of claim 1, wherein
the estimating estimates the state vector such that the state vector includes an estimate for each of a velocity of the foot in each of a first direction and a second direction, an acceleration of the foot in each of the first direction and the second direction, an angle between the foot and the ground, and an angular velocity of the foot, and
the updating updates the state vector such that the updated state vector includes a result of updating each estimate included in the state vector.

7. The method of claim 1, wherein
the variance matrix includes an estimation error covariance of each estimate in the state vector, and
the updated variance matrix includes a result of updating each estimation error covariance.

8. The method of claim 7, wherein each estimation error covariance represents a confidence of a corresponding estimate in the state vector.

9. The method of claim 1, wherein the measurement error matrix further includes (i) a measurement error variance associated with a measurement accuracy of an acceleration of the foot in each of a first direction and a second direction and (ii) an error variance associated with a measurement accuracy of an angular velocity of the foot in each of the first direction and the second direction.

10. The method of claim 1, further comprising:
generating, by the contact signal, the contact signal in response to a pressure being applied to the contact sensor.

11. A non-transitory computer-readable storage medium comprising instructions that, when executed by a processor, cause the processor to perform the method of claim 1.

12. A walking assistance device comprising:
at least one contact sensor;
an acceleration sensor; and
a controller configured to,
estimate a state vector of a foot of a user and a variance matrix corresponding to the state vector,
adjust, in response to receiving a contact signal from the at least one contact sensor, a probability of the at least one contact sensor to generate an adjusted probability based on at least one estimate included in the estimated state vector, the adjusted probability indicating a weight given to the contact signal received from the at least one contact sensor,
calculate a combination rate between a measurement value of an acceleration sensor and the state vector based on a measurement error matrix, the measurement error matrix including the adjusted probability,
update the state vector and the variance matrix to generate an updated state vector and an updated variance matrix, respectively, based on the combination rate,
determine whether the foot of the user lands on a ground based on the updated state vector and the updated variance matrix, and
change an operation mode of the walking assistance device in response determining that the foot of the user lands on the ground.

13. The walking assistance device of claim 12, wherein the controller is configured to,
perform an operation based on an estimate associated with a velocity of the foot in each of a first direction and a second direction among estimates included in the state vector, and
change the probability of the at least one contact sensor by a first error variance associated with the at least one contact sensor based on a result of the operation.

14. The walking assistance device of claim 13, wherein the controller is configured to change the probability such that the probability of the at least one contact sensor deceases.

15. The walking assistance device of claim 13, wherein the controller is configured to further change the probability by a second error variance in response to not receiving the contact signal from the at least one contact sensor after changing the probability of the at least one contact sensor by the first error variance.

16. The walking assistance device of claim 12, wherein the controller is configured to determine that the foot lands on the ground, if (i) an estimate associated with a velocity of the foot among estimates included in the updated state vector is less than a threshold velocity value and (ii) a probability of the estimate associated with the velocity among probabilities included in the updated variance matrix is less than a threshold probability.

17. The walking assistance device of claim 12, wherein the controller is configured to
estimate the state vector such that the state vector includes an estimate for each of a velocity of the foot in each of a first direction and a second direction, an acceleration of the foot in each of the first direction and the second direction, an angle between the foot and the ground, and an angular velocity of the foot, and
update the state vector such that the updated state vector includes a result of updating each estimate included in the state vector.

18. The walking assistance device of claim 12, wherein
the variance matrix includes an estimation error covariance of each estimate in the state vector, and
the updated variance matrix includes a result of updating each estimation error covariance.

19. The walking assistance device of claim 18, wherein each estimation error covariance represents a confidence of a corresponding estimate in the state vector.

20. The walking assistance device of claim 12, wherein the measurement error matrix further includes (i) a measurement error variance associated with a measurement accuracy of an acceleration of the foot in each of a first direction and a second direction and (ii) an error variance associated with a measurement accuracy of an angular velocity of the foot in each of the first direction and the second direction.

21. The walking assistance device of claim 12, wherein the at least one contact sensor is configured to generate the contact signal in response to a pressure being applied to the at least one contact sensor.

22. The walking assistance device of claim 12, wherein the acceleration sensor is configured to measure an acceleration and an angular velocity of the foot.

* * * * *